United States Patent [19]

Thulesius et al.

[11] Patent Number: 4,909,799

[45] Date of Patent: Mar. 20, 1990

[54] METHODS FOR PREVENTING THROMBOSIS; AND SURGICAL IMPLANT HAVING REDUCED PLATELET DEPOSITION CHARACTERISTICS

[76] Inventors: Olav Thulesius; Jan T. Christenson, both of P.O. Box 24923, Kuwait 13110, Kuwait

[21] Appl. No.: 98,472

[22] Filed: Sep. 18, 1987

[51] Int. Cl.$^4$ .............................................. A61M 5/325
[52] U.S. Cl. ..................................... 604/265; 514/822
[58] Field of Search ............... 514/822; 604/265, 266; 128/897, 898

[56] References Cited

U.S. PATENT DOCUMENTS

| | | | |
|---|---|---|---|
| 3,886,947 | 6/1975 | Sawyer | 604/266 |
| 4,088,659 | 5/1978 | Bhat et al. | 260/345.2 |
| 4,118,508 | 10/1978 | Bhat et al. | 424/283 |
| 4,134,986 | 1/1979 | Bajwa et al. | 424/283 |
| 4,221,805 | 9/1980 | Quadro | 514/822 |
| 4,326,532 | 4/1982 | Hammar | 604/266 |
| 4,338,325 | 7/1982 | Johnson et al. | 514/822 |
| 4,536,179 | 8/1985 | Anderson et al. | 604/266 |
| 4,588,724 | 5/1986 | Greenway, III et al. | 514/250 |
| 4,713,402 | 12/1987 | Solomon | 604/266 |
| 4,751,224 | 6/1988 | Agarwal et al. | 514/248 |

OTHER PUBLICATIONS

N. J. DeSouza, "Forskolin–An Example of Innovative Drug Research on Natural Products," *Innovative Approaches in Drug Research* 1986.
J. C. Stanley et al., "Enhanced Patency of Small–Diameter, Externally Supported Dacron Ibofemoral Grafts Seeded with Endothelial Cells," Surgery, vol. 92, No. 6, pp. 994–1005, Dec., 1982.
H. E. Kambic et al., "Biomaterials in Artificial Organs," C & EN, 4/14/86.
J. T. Christenson et al., "Surface Treatment of PTFE Grafts with Platelet Aggregation Inhibitory Drug Lowers Surface Platelet Adhesion," Int'l Soc for Cardiovascular Surg., Sep. 20–25, 1987.
Laurence A. Harker et al., "Pharmacology of Platelet Inhibitors," *JACC* vol. 8, No. 6, Dec. 1986:21B–32B.
P. Gloviczki et al., "Prevention of Platelet Deposition by Ibuprofen and Calcium Dobesilate in Expanded Polytetrafluoroethylene Vascular Grafts," *AM J. Surg* 1985;150:589–592.
Kariya et al., "Effect of Forskolin on Platelet Deaggregation and Cyclic AMP Generation," Nauyn–Schmiedeberg's *Arch Pharmacol* (1985) 331:119–121.
Two New Forskolin Analogs: P857024 and 1, 9-Dideoxy–Forskolin "International Biologics," Behring Diagnostics, A Division of American Hoechst Corporation, 1987 Number 1.
N. J. DeSouza, "Proceedings of the International Symposium on Forskolin: Its Chemical, Biological and Medical Potential," Hoechst India Limited 1985.
L. A. Harker, "Antiplatelet Drugs in the Management of Patients with Thrombotic Disorders." Seminars in Thrombosis & Hemostasis, vol. 12, No. 2, pp. 134–155–1986.
M. A. Packham et al., "Clinical Pharmacology of Platelets," Journal of Am. Soc. of Hematology, vol. 50, No. 4, pp. 555–573, 1977.
de Souza et al., "Forskolin: A Labdane Diterpenoid with Anti-hypertensive, Positive Inotropic . . .", Medicinal Research Reviews, vol. 3, No. 2, pp. 201–219, 1983.
Agarwal & Parks, "Synergistic Inhibition of Platelet Aggregation by Forskolin Plus PGE, or 2--Fluoroadenosine . . .", Biochemical Pharmacology, vol. 31, No. 22, pp. 3713–3716, 1982.
Adnot et al., "Forskolin (A Powerful Inhibitor of Human Platelet Aggregation)," Biochemical Pharmacology, vol. 31, No. 24, pp. 4074–4076, 1982.

*Primary Examiner*—C. Fred Rosenbaum
*Assistant Examiner*—Sharon Rose
*Attorney, Agent, or Firm*—Banner, Birch, McKie & Beckett

[57] ABSTRACT

In order to improve the surface properties of small caliber vascular grafts or other surgical implants, Forskolin (or a derivative thereof) which is a power cAMP stimulating agent, is applied to the thrombogenic surfaces of the graft/implant. Forskolin as thus used is a potent antiplatelet agent significantly lowering platelet deposition on the implant.

34 Claims, 2 Drawing Sheets

METHODS FOR PREVENTING THROMBOSIS; AND SURGICAL IMPLANT HAVING REDUCED PLATELET DEPOSITION CHARACTERISTICS

BACKGROUND OF THE INVENTION

Thrombosis of artificial graft surfaces in small caliber vessels is a major problem in both cardiac and peripheral vascular surgery. Synthetic vascular grafts are inherently thrombogenic and, when prosthetic material is used to bypass medium-sized or small arteries, thrombotic obstruction is a major problem. Although the systemic administration of plateletaggregation inhibitory or anticoagulant drugs has been generally successful, considerable difficulties and the disadvantages of side effects have been experienced. See, P. Gloviczki, et al., "Prevention of Platelet Deposition by Ibuprofen and Calcium Dobesilate in Exapanded Polytetrafluoroethylene Vascular Grafts," *AM J Surg* 1985;150:589–592. The contents of this and each of the other documents and articles mentioned herein are hereby incorporated by reference in heir entireties. See also Laurence A. Harker et al, "*Pharmacology of Platelet Inhibitors,*" JACC Vol. 8, No. 6, Dec. 1986:21B–32B. Also, endothelial seeding of graft surfaces to reduce blood clotting is a tedious and expensive procedure. See, e.g., J. C. Stanley et al., "Enhanced Patency of Small-Diameter, Externally Supported Dacron Ibofemoral Grafts Seeded with Endothelial Cells," *Surgery*, Vol. 92, No. 6, pp 994–1005, Dec., 1982. Further problems encountered with artificial organs are discussed in H. E. Kambic, et al., "Biomaterials in Artificial Organs," C & EN, 4/14/86. Accordingly a need has arisen for an improved method for reducing the incidence of thrombosis resulting from surgical implants which method is simple, relatively inexpensive, and does not have side effects and problems experienced with the prior methods.

The structure of Forskolin is 7B-acetoxy-8, 13-epoxy-1a, 6B, 9a-trihydroxylabd-14-en-11-one.

Figure 2:
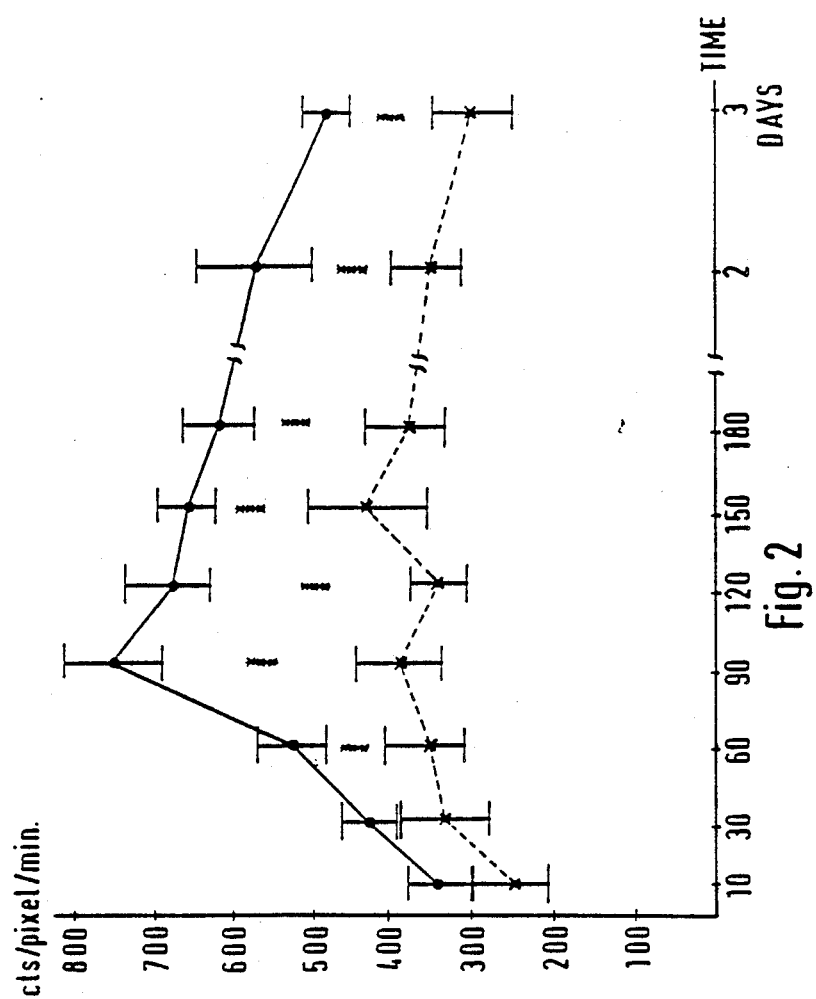

FIG. 2 is a graph showing the results of an Example conducted to illustrate the present invention.

The platelet uptake onto graft surfaces is illustrated. The graft activity plus or minus time curves of x—x Forskolin impregnated PTFE grafts and o—o untreated control grafts. (mean plus or minus SD). ** p less than 0.001.

DETAILED DISCUSSION OF THE INVENTION

This invention satisfies those needs and its procedure is very straightforward. Before the surgical implants, such as vascular grafts, cardiac assist devices, artificial hearts, and the like, are implanted in the patient, Forskolin or a derivative or an analog thereof is applied to the thrombogenic (blood-clot forming) surfaces of the implant.

Figure 1:
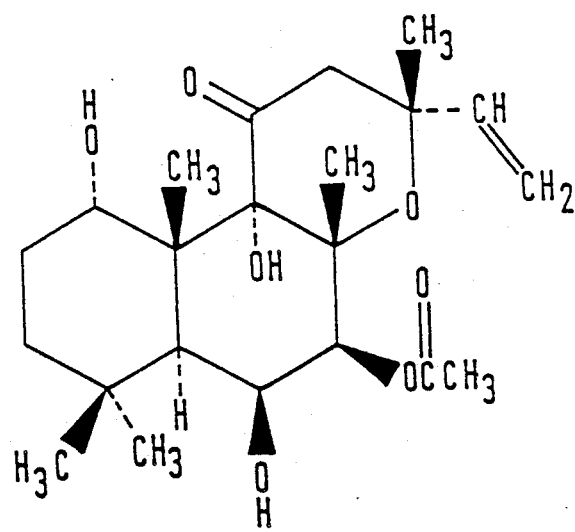
FIG. 1 illustrates the chemical structure of the drug of the present invention.

Forskolin is a relatively new biologically active natural product discovered at the Hoechst Research Center in India, which is a subsidiary of the German pharmaceutical company of the same name (Hoechst, Frankfurt). In the United States, the drug is distributed by Calbiochem of San Diego, which is a division of the American Hoechst Corporation. See N. J. DeSouza, "Forskolin-An Example of Innovative Drug Research on Natural Products," Innovative Approaches in Drug Research 1986, wherein it was reported that this drug has been introduced in human trials for the treatment of cardiac insufficiency, glaucoma and asthma. Forskolin is the naturally occurring diterpene isolated from the roots of Coleus forskoli extracted and purified, and is one of the most powerful cyclic adensine monophosphate (cAMP) stimulators with cardiac inotropic, vasodilator and platelet stabilizing properties. See A. M. Siegl et el., "Inhibition of Aggregation and Stimulation of Cyclic AMP Generation in Intact Human Platelets by Diterpene Forskolin," *Molecular Pharmac* 1982;21:680. The structure of Forskolin is illustrated in FIG. 1 and has been shown to be 7B-acetoxy-8, 13-epoxy-1a, 6B, 9a-trihydroxylabd-14-en-11-one. See N. J. DeSouza, "Proceedings of the International Symposium on Forskolin: Its Chemical, Biological and Medical Potential," Hoechst India Limited 1985 Derivatives of Forskolin are mentioned in the DeSouza 1986 article and analogs P857024 and 1, 9-Dideoxy-Forskolin are discussed in "International Biologics," Behring Diagnostics, a Division of American Hoechst Corporation, 1987 Number 1.

The active principle, Forskolin, and/or one or more of its derivatives, (such as 7-0-he-misuccinyl-7-deacetyl-forskolin, P 8570249 (Hoechst-Roussel)), is thus applied locally to the thrombogenic surface of the implant by a suitable bonding procedure, to assure satisfactory contact with the implant for a sufficient time and to maintain the activity of the Forskolin molecule. For example, the graft can be soaked in a 0.05-0.15% or preferably a 0.1% alcoholic solution of Forskolin and then left to dry at room temperature before being implanted. Alternatively, the drug can be bound (covalently) to polyurethane (PU), polyethylene add poly-L-lactic acid. (PU and PE derivatives). Thereby the antiplatelet theory of the present invention is restricted to the implant/ graft itself. A model experiment for this invention has been conducted in sheep by monitoring blood flow and platelet deposition in polytetrafluoroethylene (PTFE) grafts, and is discussed in detail below.

EXAMPLE

1. Materials and Method

Twenty PTFE (GORE TEX) standard type grafts were implanted into the superficial femoral arteries of ten apparently healthy, male Australian sheep weighing 30-40 kg. Prior to induction of anaesthesia, 40 ml of venous blood were withdrawn in acid citrate dextrose (ACD) for labelling of the platelets. Anaesthesia was then induced by an intravenous injection of sodium thiopentone (INTRAVAL, May & Baker Ltd., England), at twenty-five mg/kg of the animal's bodyweight. After endotracheal intubation the animals were ventilated with room air using a Harvard animal ventilator (Harvard Apparatus Co, USA) and anaesthesia was maintained with continuous intravenous infusion of ketamine (KETALAR, Parke Davis Ltd., England), at three mg/kg/hr. No heparn (or other anticoagulant) was administered at any time.

Both superficial femoral arteries were exposed, using sterile surgical techniques, and all surgical procedures herein were done by one surgeon. On both sides a five cm long standard PTFE graft having an inner diameter of four mm, was interposed with continuous 6/0 PROLENE (Ethicon, England) sutures. On one side the graft was pretreated with a 0.1 mg/ml ethanol Forskolin solution, and the Forskolin impregnated graft was left to dry before implantation thereof. On the other side an untreated graft was placed as a control.

During surgery the autologous platelets were isolated and labelled with Indium-111-oxine (Amersham Ltd., England) according to previously described techniques. See J. T. Christenson et al., "A Comparison of Two methods of Labelling Autologous Platelets with 111-In-oxine in Five Different Species," *European J. Nucl Med.* 1983;8:389–392. After the grafts were in place, but before they were exposed to blood, the labelled platelets were re-infused intravenously. The injected activity was 220 ±75 uCi and the labelling efficiency was 88 ±6%. The animals were placed in supine position under a gamma camera (General Electrics, 400 AT) which was linked to a STAR computer. A medium energy collimator was used and the energy window of the gamma camera was set at 10% including both energy peaks of In-111. Ten minutes after reestablishing blood flow continuous gamma camera aquisition was obtained for tree hours. Blood flow through the grafts was monitored with a noncannulating square wave electromagnetic blood flow meter (SP 2202, Gould Co., USA) and two mm sized flow probes. For two consecutive days the animals were shortly anaesthetized with ketamine and a gamma camera image was obtained. At the end of the experiment the grafts were harvested, their activity counted in a well counter and then submitted to histopathological examination.

Repeated blood samples were taken for platelet counting and activity measurement in well counter throughout the experiment.

2. Data analysis

From the nuclear images actual graft activity was calculated from different regions of interest as graft activity minus blood activity corrected for background activity and physical decay of the radioisotope. Thereafter graft activity time curves for Forskolin impregnated and control grafts were respectively generated.

3. Results

All grafts were found to be patent at the end of the observation period. The first experiment which was performed with a graft, soaked in a concentration of Forskolin ten times higher than the subsequent experiments, had to be terminated because of severe bleeding from the anastomotic suture lines. Platelet deposition onto the surfaces of the control and treated grafts as evaluated repeatedly in vivo by monitoring radioactivity with gamma camera is presented in FIG. 2. This graph shows a rapid continuous build-up of activity over both sides which peaks at one hundred minutes with a consequent decline. Moreover it can be seen that during the whole observation period there was significantly less deposition of platelets on the Forskolin-treated side.

Monitoring of platelet counts and radioactivity of venous blood samples showed a decline over the first three hours, followed by a subsequent elevation. Arterial blood flow through the grafts, as shown below in Table I, gave about equal readings on both sides.

TABLE I

| Blood flow (ml/min) through vascular grafts after implantation in different groups. (Mean ± SD) | |
|---|---|
| | Blood flow, ml/min |
| Forskolin impregnated | 158 ± 31 |

TABLE I-continued

| Blood flow (ml/min) through vascular grafts after implantation in different groups. (Mean ± SD) | |
|---|---|
| | Blood flow, ml/min |
| PTFE grafts (N = 10) Untreated control PTFE grafts (N = 10) | 163 ± 40 |

Graft activity as counted in a well counter in vitro confirmed the in vivo obtained differences with significantly higher activity counts in the control PFTE graft, 43048±1506 cts/min, compared to 19102±1396 cts/min for the Forskolin treated grafts, $p<0.001$. The histopathological examination of the grafts also showed the same differences in platelet deposition.

4. Discussion

Prosthetic materials such as PTFE grafts have a thrombogenic surface and initial platelet deposition peaks at 100 to 130 minutes after reestablishment of blood flow through the graft. See J. T. Christenson et al., "The Effect of Blood Flow Rates on Platelet Deposition in PTFE Arterial Bypass Grafts," Trans Am Soc Artif Intern organs 1981;27:188–190. This is probably the result of a balance between maximum platelet deposition and removal from the luminal surface as the result of adhesion and shear forces of the flowing blood. It has been demonstrated that the initial exposure period of the graft after reestablishment of flow is critical to the ultimate result, since large platelet deposition may result in thrombosis and occlusion. See P. Gloviczki et al., "Prevention of Platelet Deposition by Ibuprofen and Calcium Dobesilate in Expanded Polytetrafluoroethylene Vascular Grafts," *AM J Surg* 1985;150:589–592. Local treatment of the graft surface to prevent undue platelet deposition should be an ideal solution to this problem, as this invention proves.

The mode of action of Forskolin is unlike all other cAMP stimulators; it does not interact with beta-adrenergic receptors nor does it inhibit the breakdown of cAMP such as the platelet-stabilizer dipyramidole. The mechanism of action has not yet been entirely clarified but it seems that Forskolin activates the enzyme adenylate cyclase which is responsible for the conversion of ATP to cAMP. I addition to the direct stimulation of this enzymatic reaction Forskokin is also reported to augment endogenous hormones which normally stimulate cAMP levels. See A. B. Seamon et al., "Forskolin: Unique Diterpene Activator of Adenylate Cyclase in Membranes and Intact Cells," Proc.Natl.Acad.Sci.USA 1981;78:3363; N. J. DeSouza, "Forskolin An Example of Innovative Drug Research on Natural Products." In: Innovative Approaches in Drug Research. *Harma AF ed*, Elsevier Sc.Publ. Amsterdam 1986, pp 191–207. Agents which raise cAMP levels inhibit all platelet reactions. By analogy with the effects of cAMP in smooth muscle, it has been suggested that this causes the sequestration of calcium in the cytoplasm which inhibits the contractile response associated with the platelet release reaction. See M. A Packham et al., "Clinical Pharmacology of Platelets," *Blood* 1977;50:555–573. Although only the first three days after graft implantation were studied, the initial days after implantation are of critical importance for the outcome of graft patency. Thus, Forskolin when applied to the inner surface of an arterial prosthesis has been proven to be a potent antiplatelet agent.

The treatment of the present invention can be used in vascular surgery on the arterial and venous sides and for artificial heart assist devices in which clotting is still major problem. It can also be employed in coronary artery bypass surgery where approximately 500,000 cases are performed annually. Therapeutic arteriovenous shunts, ventricular assist devices and artificial valves can all be treated prior to implantation according to this invention.

Forskolin has the added advantage in that it acts synergistically with agents which prevent platelet aggregation, such as prostaglandins. As noted in Kariya et al., "Effect of Forskolin on Platelet Deaggregation and Cyclic AMP Generation," Nauyn-Schmiedeberg's *Arch Pharmacol* (1985) 331:119–121, this effect seems to be more than additive. That article however simply clarifies the molecular mechanism of action of Forskolin (cyclic AMP stimulation alone or additional mechanism). If the proper concentration of the Forskolin solution is used, no disadvantages or side effects such as bleeding complications are expected, and resulting bleeding is a major problem of conventional systemic treatment with known anticoagulants such as coumarine, warfarine, and acetylsalicylic acid. Since the local application technique of this invention requires only a low dose of Forskolin, harmful elevation of the patient's heart rate or enhancement of his blood sugar are not expected to result.

Forskolin adheres best and allows for longer contact to coarser types of implant surfaces such as woven meshes or textures, than to slippery types of surfaces. Additionally and ideally only the surfaces of the graft exposed to flowing blood should be coated, and the surfaces exposed to tissue (unlike in the previously discussed soaking or dipping procedure) should not be treated. It is also within the scope of this invention to chemically bind the Forskolin or a derivative thereof directly to the thrombotic surface of the implant/graft to ensure its staying power and to prolong its effect, but care should be taken in this binding procedure to not alter or reduce the efficacy of the active groups of the Forskolin molecule. Substances, such as Araldite and Epon resins, which are compatible with Forskolin and the graft surfaces, should be tried. Further this invention contemplates for the manufacturer to apply this Forskolin coating to the inside of the synthetic implant/graft before it is packed and distributed and in a method to ensure its stability to facilitate the handling thereof and to make the surgical procedure easier.

In addition to inhibiting the formation of blood clotting, it is within the scope of this invention to treat existing blood clots, such as those forming from implants, e.g. arterial grafts. In the case of graft thrombosis a 0.05% Forskolin in a 30% ethanol/physiological saline solution can be administered intravascularly to the patient and upstream of the blood clot. The injection can be repeated under the control of the patient's heart rate and by non-invasive monitoring of his blood flow with a Doppler flowmeter. Prostaglandins such as Prostacylin (PG1-2) or PGE-2, can be used in conjunction with this Forskolin injection treatment since there is evidence that this can potentiate the anticoagulant effect of Forskolin, as mentioned above.

From the foregoing detailed description it will be evident that there are a number of changes, adaptations, and modifications of the present invention which come within the province of those skilled in the art. However, it is intended that all such variations not departing from the spirit of the invention be considered as within the scope thereof as limited solely by the appended claims.

What is claimed is:

1. A method for reducing the incidence of thrombosis in a patient following a surgical implant procedure on the patient comprising the steps of:
   applying 7B-acetoxy-8,13-epoxy-1a-6B,9a-trihydroxylabd-14-en-11-one (Forskolin) or a derivative thereof to a surgical implant, and
   thereafter, implanting the surgical implant with the Forskolin or a derivative thereof thereon into the patient.

2. The method of claim 1 including,
   said applying including soaking the surgical implant in the Forskolin or a derivative thereof.

3. The method of claim 2 including,
   said soaking including soaking the surgical implant in a solution of the Forskolin or a derivative thereof.

4. The method of claim 3 including,
   said solution being an alcohol solution.

5. The method of claim 3 including,
   said solution including ethanol.

6. The method of claim 5 including,
   said solution being 96% ethanol.

7. The method of claim 3 including,
   said solution having a strength of 0.05–0.15% of the Forskolin or a derivative thereof.

8. The method of claim 7 including,
   said solution comprising 0.1% alcoholic solution of the Forskolin or a derivative thereof.

9. The method of claim 3 including,
   said solution comprising an organic solvent.

10. The method of claim 9 including,
    said organic solvent having affinity characteristics to polyurethane or polyethylene.

11. The method of claim 3 including,
    said applying including after said soaking, and before said implanting, drying the implant.

12. The method of claim 11 including,
    said drying including allowing the implant to dry at room temperature.

13. The method of claim 1 including,
    said Forskolin or a derivative thereof comprising 7-0-he-misuccinyl-7-deacety-forskolin.

14. The method of claim 1 including,
    said Forskolin or a derivative thereof being chemically bound to polyurethane, polyethylene, or poly-L-lactic acid before being applied to the implant.

15. The method of claim 1 including,
    said implant comprising a by-pass graft, an artificial cardiac implant, or a therapeutic arteriovenous shunt.

16. The method of claim 1 including,
    said applying including coating the surface of the implant which will be in contact with blood with the Forskolin or a derivative thereof to prevent platelet aggregation thereon.

17. The method of claim 1 further comprising,
    applying to the implant an agent that acts synergistically with the Forskolin or the derivative thereof to prevent platelet aggregation.

18. The method of claim 17 including
    said agent comprising a prostaglandin.

19. The method of claim 1 including,
    said implant comprising a transplant from the patient.

20. The method of claim 19 including, before said coating, removing the transplant from the patient.

21. The method of claim 20 including,
said transplant comprising an autologous vein graft, and
said Forskolin or a derivative thereof being applied in an isotonic solution.

22. The method of claim 1 including,
said Forskolin or a derivative thereof comprising Forskolin.

23. A method for preventing undue platelet aggregation on a synthetic vascular graft used in cardiovascular surgery on a patient comprising the steps of:
before implanting the synthetic vascular graft in the patient, applying locally to the graft 7B-acetoxy-8, 13-epoxy-1a-6, 9a-trihydroxylabd-14-en-11-one (Forskolin) or a derivative thereof.

24. The method of claim 1 including,
said implant comprising a synthetic vascular graft.

25. An implant device suitable for surgical implantation in a patient and showing low resulting platelet deposition thereon comprising:
a surgical implant having an implant thrombogenic surface, and
a coating of 7B-acetoxy-8,13-epoxy-1a-6B,9a-trihydroxylabd-14-en-11-one (Forskolin) or a derivative thereof on said implant thrombogenic surface.

26. The implant device of claim 25 including,
said coating being applied to said implant thrombogenic surface before said surgical implant is implanted in the patient.

27. The implant device of claim 25 including,
said surgical implant being formed of a synthetic material.

28. The implant device of claim 27 including,
said synthetic material being polytetrafluoroethylene.

29. The implant device of claim 25 including,
said surgical implant comprising a transplant from the patient.

30. The implant device of claim 25 including,
said surgical implant comprising a vascular graft, a cardiac implant, a cardiac assist device, or an artificial device.

31. The implant device of claim 25 including,
said surgical implant comprising an auto-transplanted vessel.

32. The implant device of claim 25 including,
said coating being applied b soaking said implant in a solution of the Forskolin or a derivative thereof and thereafter drying said implant before implanting said implant in the patient.

33. The implant device of claim 25 including,
said surgical implant being a polytetrafloroethylene graft.

34. The implant device of claim 25 including,
said surgical implant comprising a synthetic vascular graft four millimeters or less in diameter and greater than eight centimeters in length.

* * * * *